United States Patent [19]

Stoltefuss et al.

[11] Patent Number: 5,262,429

[45] Date of Patent: Nov. 16, 1993

[54] ARYL-QUINOLYL-SUBSTITUTED 1,4-DIHYDROPYRIDINE-DICARBOXYLIC ACID COMPOUNDS WHICH HAVE USEFUL PHARMACEUTICAL UTILITY

[75] Inventors: Jürgen Stoltefuss, Haan; Siegfried Goldmann, Wuppertal; Alexander Straub, Wuppertal; Rainer Gross, Wuppertal; Martin Bechem, Wuppertal; Siegbert Hebisch, Wuppertal; Joachim Hütter, Wuppertal; Howard-Paul Rounding, Wuppertal, all of Fed. Rep. of Germany

[73] Assignee: Bayer Aktiengesellschaft, Leverkusen, Fed. Rep. of Germany

[21] Appl. No.: 959,843

[22] Filed: Oct. 13, 1992

[30] Foreign Application Priority Data

Oct. 22, 1991 [DE] Fed. Rep. of Germany ....... 4134760

[51] Int. Cl.$^5$ ................... C07D 401/04; A61K 31/47
[52] U.S. Cl. ..................................... 514/314; 546/167
[58] Field of Search ............... 546/153, 156, 157, 167, 546/169, 170; 514/312, 314

[56] References Cited

U.S. PATENT DOCUMENTS

| | | | |
|---|---|---|---|
| 3,855,231 | 12/1974 | Meyer et al. | 260/294.8 |
| 3,860,601 | 1/1975 | Meyer et al. | 260/294.8 |
| 3,887,558 | 6/1975 | Meyer et al. | 260/294.8 |
| 3,907,808 | 9/1975 | Lesher et al. | 546/156 |
| 3,932,645 | 1/1976 | Meyer et al. | 424/266 |
| 3,946,026 | 3/1976 | Meyer et al. | 260/295.5 |
| 3,950,336 | 4/1976 | Meyer et al. | 260/294.8 |
| 3,957,998 | 5/1976 | Meyer et al. | 260/294.8 |
| 3,959,474 | 5/1976 | Meyer et al. | 260/294.8 |
| 3,988,458 | 10/1976 | Meyer et al. | 514/269 |
| 4,002,762 | 1/1977 | Meyer et al. | 424/266 |
| 4,016,277 | 4/1977 | Meyer et al. | 260/287 |
| 4,049,662 | 9/1977 | Meyer et al. | 260/287 |
| 4,145,432 | 3/1979 | Sato | 424/266 |
| 4,248,873 | 2/1981 | Bossert et al. | 424/256 |
| 4,948,899 | 8/1990 | Ogawa et al. | 546/321 |
| 5,100,900 | 3/1992 | Stoltefuss et al. | 514/314 |

FOREIGN PATENT DOCUMENTS

| | | | |
|---|---|---|---|
| 0288758 | 3/1988 | European Pat. Off. | 546/153 |
| 2117571 | 4/1971 | Fed. Rep. of Germany | 546/153 |
| 2210667 | 3/1972 | Fed. Rep. of Germany | 546/153 |
| 4011105 | 4/1990 | Fed. Rep. of Germany | 546/153 |
| 1173862 | 3/1968 | United Kingdom | 546/313 |

OTHER PUBLICATIONS

A. Fleckenstein, *Ann. Rev. Pharmacol. Toxicol.*, 1977, pp. 149–166.
Norman Levy, *J. Chem. Soc.*, 1946, pp. 1100–1104.
Charles D. Hurd, *J. Org. Chem.*, 1955, pp. 927–936.
Samuel A. Glickman, *J. Am. Chem.*, 1945, pp. 1017–1020.
L. H. Opie, *J. Physiol.*, 1965, pp. 529–541.

*Primary Examiner*—C. Warren Ivy
*Assistant Examiner*—Zinna N. Davis
*Attorney, Agent, or Firm*—Sprung Horn Kramer & Woods

[57] ABSTRACT

The invention relates to novel aryl-quinolyl-substituted 1,4-dihydropyridine-di-carboxylic acid derivatives, to processes for their preparation and to their use in drugs, especially for the preparation drugs for the treatment of cardiovascular diseases.

8 Claims, No Drawings

ARYL-QUINOLYL-SUBSTITUTED 1,4-DIHYDROPYRIDINE-DICARBOXYLIC ACID COMPOUNDS WHICH HAVE USEFUL PHARMACEUTICAL UTILITY

The invention relates to novel aryl-quinolyl-substituted 1,4-dihydropydridine-dicarboxylic acid derivatives, to processes for their preparation and to their use in drugs, especially for the preparation of drugs for the treatment of cardiovascular diseases.

It is already known that 1,4-dihydropyridines possess vasodilating properties and can be used as coronary drugs and antihypertensives [cf. British patent 1 430 926]. It is further known that 1,4-dihydropyridines inhibit the contractility of smooth and cardiac muscles and can be used for the treatment of coronary and vascular diseases [cf. Fleckenstein, Ann. Rev. Pharmacol. Toxicol., 17, 149–166 (1977)].

It is also known that 1,4-dihydropyridines having a 3,5-diester, 3,5-diacyl or 3,5-ester/acyl grouping act as calcium antagonists [cf. German Offenlegungsschrift 37 11 991].

4-Quinolyl-1,4-dihydropyridines with other structures are also known from German Offenlegungsschrift 22 10 667 and German Offenlegungsschrift 22 10 687.

The present invention relates to aryl-quinolyl-substituted 1,4-dihydropyridine-dicarboxylic acid derivatives of general formula (I):

$$R_4-X-OC \diagdown \diagup CO-X-R_3 \quad (I)$$
(with $R_5$ at 4-position, $R_1$, $R_2$ at 2,6, N-H)

in which

R$^1$ and R$^2$ are identical or different and are hydrogen or linear or branched alkyl having up to 6 carbon atoms, or one of the two substituents R$^1$ or R$^2$ is the —NH$_2$ group, X is an oxygen atom or the —NH— group, R$^3$ and R$^4$ are identical or different and are hydrogen or cycloalkyl having 3 to 6 carbon atoms, or are linear or branched alkenyl or alkyl each having up to 10 carbon atoms which may be interrupted by an oxygen or sulphur atom in the chain and/or are unsubstituted or substituted by carboxyl, halogen, cyano, hydroxyl, phenyl, phenoxy or benzyloxy, or by linear or branched alkoxy, acyl or alkoxycarbonyl each having up to 8 carbon atoms, or by a group of the formula —NR$^6$R$^7$, wherein R$^6$ and R$^7$ are identical or different and are hydrogen, linear or branched alkyl having up to 6 carbon atoms, benzyl or phenyl, and R$^5$ is a radical of the formula (quinoline structures with $R_8$ and $R_9$ substituents)

wherein

R$^8$ is hydrogen, halogen or linear or branched alkyl or alkoxy each having up to 6 carbon atoms, and R$^9$ is aryl having 6 to 10 carbon atoms which is unsubstituted or substituted by up to 3 identical or different substituents selected from the group comprising halogen, nitro, cyano, trifluoromethyl, trifluoromethoxy and trifluoromethylthio, or by linear or branched alkyl having up to 8 carbon atoms, which in turn can be substituted by aryl having 6 to 10 carbon atoms, or by linear or branched alkoxy or alkoxycarbonyl each having up to 8 carbon atoms, by carboxyl, or by a group of the formula —NR$^6$R$^7$, wherein R$^6$ and R$^7$ are as defined above, or R$^9$ is 2- or 3-thienyl which is unsubstituted or substituted by halogen, and their physiologically acceptable salts.

Physiologically acceptable salts are salts of the compounds according to the invention with inorganic or organic acids. Preferred salts are those with inorganic acids such as, for example, hydrochloric acid, hydrobromic acid, phosphoric acid or sulphuric acid, or those with organic carboxylic or sulphonic acids such as, for example, acetic acid, maleic acid, fumaric acid, malic acid, citric acid, tartaric acid, lactic acid, benzoic acid, methanesulphonic acid, ethanesulphonic acid, phenylsulphonic acid, toluenesulphonic acid or naphthalenedisulphonic acid.

The compounds according to the invention exist in stereoisomeric forms which either behave like image and mirror image (enantiomers) or do not behave like image and mirror image (diastereoisomers). The invention relates to both the antipodes and, the racemic forms, as well as the mixtures of diastereoisomers. The racemic forms, like the diastereoisomers, can be resolved in known manner into the stereoisomerically pure components (cf. E.L. Eliel, Stereochemistry of Carbon Compounds, McGraw Hill, 1962).

Preferred compounds of general formula (I) are those in which

R$^1$ and R$^2$ are identical or different and are hydrogen or linear or branched alkyl having up to 4 carbon atoms, or one of the two substituents R$^1$ or R$^2$ is the —NH$_2$ group, X is an oxygen atom or the —NH— group, R$^3$ and R$^4$ are identical or different and are hydrogen, cyclopropyl, cyclopentyl or cyclohexyl, or are linear or branched alkenyl or alkyl each having up to 8 carbon atoms which may be interrupted by an oxygen or sulphur atom in the chain and/or are unsubstituted or substituted by carboxyl, halogen, cyano, hydroxyl or phenyl, or by linear or branched alkoxy, acyl or alkoxycarbonyl each having up to 6 carbon atoms, or by a group of the formula —NR$^6$R$^7$, wherein $R^6$ and $R^7$ are identical or different and are hydrogen, linear or branched alkyl having up to 4 carbon atoms, or benzyl, and $R^5$ is a radical of the formula

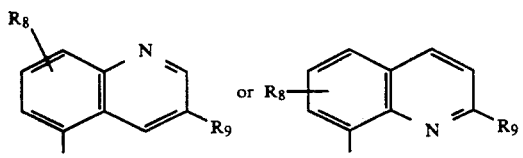

wherein $R^8$ is hydrogen, halogen or linear or branched alkyl or alkoxy each having up to 4 carbon atoms, and $R^9$ is phenyl which is unsubstituted or substituted by up to 2 identical or different substituents selected from the group comprising halogen; nitro, cyano and trifluoromethyl, or by linear or branched alkyl or alkoxy each having up to 6 carbon atoms, by benzyl or by a group of the formula $-NR^6R^7$, wherein $R^6$ and $R^7$ are as defined above, or $R^9$ is 2- or 3-thienyl which is unsubstituted or substituted by halogen, and their physiologically acceptable salts.

Particularly preferred compounds of general formula (I) are those in which $R^1$ and $R^2$ are identical or different and are hydrogen, methyl, ethyl, propyl or isopropyl, or one of the two substituents $R^1$ or $R^2$ is the $-NH_2$ group, X is an oxygen atom or the $-NH-$ group, $R^3$ and $R^4$ are identical or different and are hydrogen, cyclopropyl, cyclopentyl or linear or branched alkyl having up to 6 carbon atoms, which is unsubstituted or substituted by carboxyl, fluorine, chlorine, cyano or hydroxyl, or by linear or branched alkoxy, acyl or alkoxycarbonyl each having up to 4 carbon atoms, or by a group of the formula $-NR^6R^7$, wherein $R^6$ and $R^7$ are identical or different and are hydrogen, methyl, ethyl or benzyl, and $R^5$ is a group of the formula

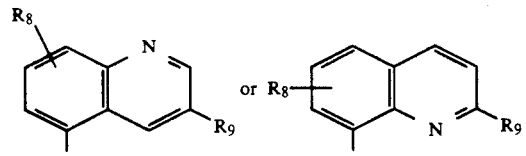

wherein $R^8$ is hydrogen, ethyl or methyl, and $R^9$ is phenyl which is unsubstituted or substituted by up to 2 identical or different substituents selected from the group comprising fluorine, chlorine nitro and trifluoromethyl, or by linear or branched alkyl or alkoxy each, having up to 4 carbon atoms, or by a group of the formula $-NR^6R^7$, wherein $R^6$ and $R^7$ are as defined above, or $R^9$ is 2- or 3-thienyl, and their physiologically acceptable salts.

The invention further relates to processes for the preparation of the compounds of general formula (I) according to the invention, characterised in that

[A] aldehydes of general formula (II):

$$R^5-CHO \qquad (II)$$

is as defined above, $R^5$ is as defined above, are first reacted with acetoacetic acid derivatives of general formula (III):

$$R^2-CO-CH_2-CO-X-R^3 \qquad (III)$$

in which $R^3$ and X are as defined above, and $R^{2'}$ is as defined above for $R^2$, but is not amino, if appropriate with isolation of the corresponding ylidene compound of general formula (IV):

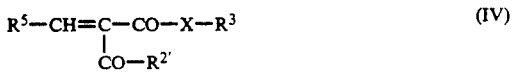

in which $R^{2'}$, $R^3$, $R^5$ and X are as defined above, and then reacted either with compounds of general formula (V):

$$R^{1'}-CO-CH_2-CO-X-R^4 \qquad (V)$$

in which $R^4$ and X are as defined above, and $R^{1'}$ is as defined above for $R^1$, but is not amino, in the presence of ammonia or ammonium salts, or directly with the enamines formed therefrom of general formula (VI):

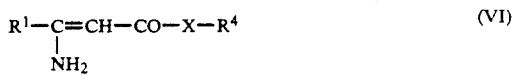

in which $R^1$, $R^4$ and X are as defined above, if appropriate in the presence of inert organic solvents, or

[B] the aldehydes of general formula (II) are first reacted with compounds of general formula (V), if appropriate with isolation of the ylidene compounds of general formula (VII):

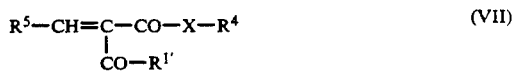

in which $R^{1'}$, $R^4$, $R^5$ and X are as defined above, and reacted in a subsequent step with compounds of general formula (III) in inert solvents, in the presence of ammonia or ammonium salts, or directly with the enaminocarboxylic acid derivatives of general formula (VIII):

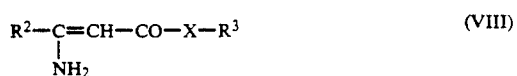

in which $R^2$, $R^3$ and X are as defined above, or

[C] in the case where $R^4$ is not hydrogen, compounds of general formula (I) in which $R^1$, $R^2$ and $R^5$ are as defined above and $R^3$ is hydrogen are reacted with the appropriate alcohols or amines, if appropriate via a reactive acid derivative, the use of the enantiomerically pure derivatives ($R^3$=H) giving the corresponding enantiomers of the compounds of formula (I).

The processes according to the invention can be exemplified by the following reaction scheme:

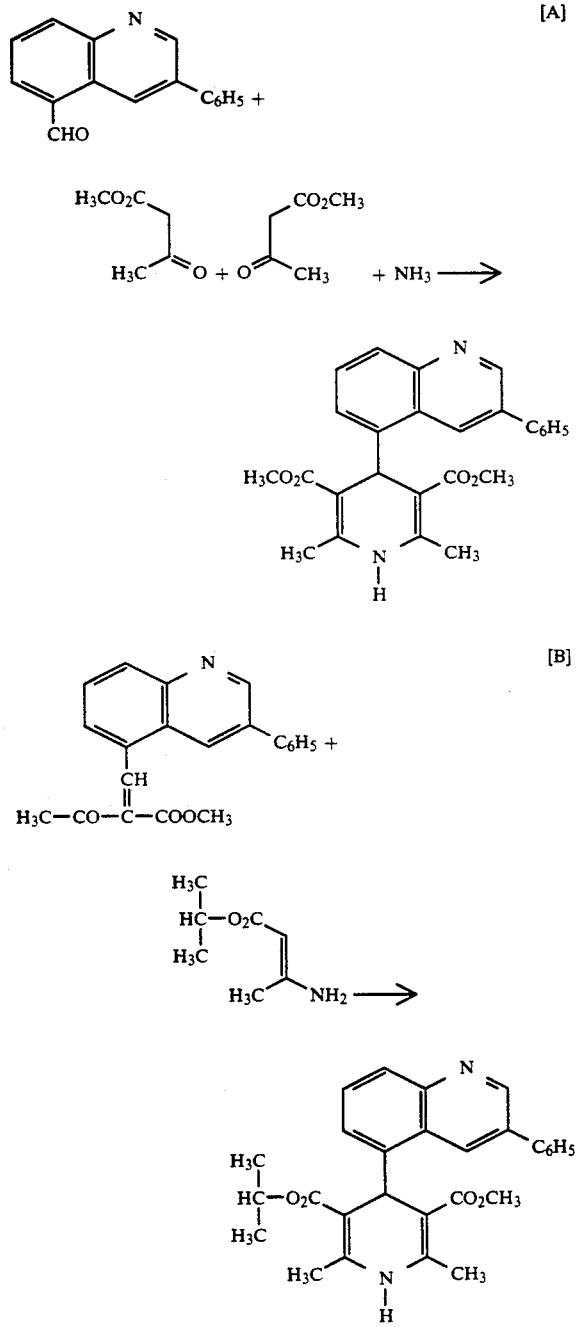

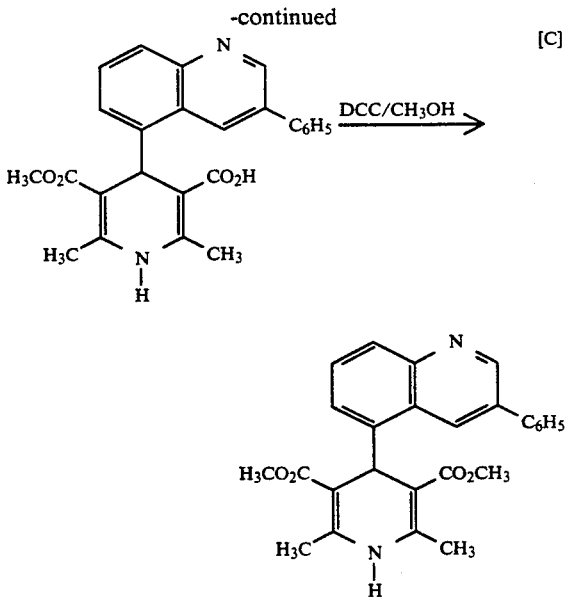

Suitable solvents for processes [A] and [B] are all inert organic solvents which do not change under the reaction conditions. These preferably include alcohols such as methanol, ethanol, propanol or isopropanol, ethers such as diethyl ether, dioxane, tetrahydrofuran, glycol dimethyl ether or diethylene glycol dimethyl ether, acetonitrile, amides such as hexamethylphosphorotriamide or dimethylformamide, acetic acid, halogenated hydrocarbons such as methylene chloride or carbon tetrachloride, or hydrocarbons such as benzene or toluene. It is also possible to use mixtures of said solvents. Depending on the particular process variant [A] or [B], it is preferable to use methanol, isopropanol, ethanol and n-propanol, acetonitrile or tetrahydrofuran.

Suitable solvents for process [C] are those listed above, with the exception of alcohols.

The reaction temperatures can be varied within wide limits. The reaction is generally carried out at between +10° C. and +150° C., preferably at between +20° C. and +100° C. and especially at the boiling point of the solvent in question.

The reaction can be carried out at normal pressure or else at elevated or reduced pressure (e.g. 0.5 to 3 bar). It is generally carried out at normal pressure.

When carrying out the processes according to the invention, it is possible to use any desired proportions of the substances participating in the reaction. In general, however, the reaction is carried out with molar amounts of the reactants.

Suitable reagents for activating the carboxylic acid are the conventional reagents such as inorganic halides, for example thionyl chloride, phosphorus trichloride or phosphorus pentachloride, carbonyldiimidazole, carbodiimides such as cyclohexylcarbodiimide or 1-cyclohexyl-3-[2-(N-methylmorpholino)ethyl]-carbodiimide-p-toluene-sulphonate, N-hydroxyphthalimide or N-hydroxy-benzo-triazole.

Enantiomerically pure forms are obtained e.g. by resolving mixtures of diastereoisomers of the compounds of general formula (I) in which $R^4$ is an optical ester radical, by a conventional method, then either transesterifying directly or first preparing the chiral carboxylic acids and then, if appropriate, preparing the enantiomerically pure dihydropyridines by esterification or amidation.

Suitable chiral ester radicals are all esters of enantiomerically pure alcohols such as, for example, 2-butanol, 1-phenylethanol, lactic acid, lactic acid esters, mandelic acid, mandelic acid esters, 2-amino-alcohols, sugar derivatives, hydroxyamino acid derivatives and many other enantiomerically pure alcohols.

The diastereoisomers are generally resolved either by fractional crystallisation, or by column chromatography, or by Craig partition. Which process is optimal must be decided in each particular case; sometimes it is also convenient to use combinations of, the individual processes. It is particularly suitable to carry out the resolution by crystallisation or Craig partition or by a combination of both processes.

The compounds of general formula (II) are known in some cases and can be prepared by conventional methods, e.g. by oxidising the corresponding alkyl- or hydroxyalkyl-quinolines or reducing the corresponding carboxy-quino-lines (cf. also German Offenlegungsschrift 40 11 105).

The acetoacetic acid derivatives of formula (III) are known or can be prepared by conventional methods [cf. D. Borrmann, "Umsetzung von Diketonen mit Alkoholen, Phenolen und Mercaptanen" ("Reaction of diketones with alcohols, phenols and mercaptans"), in Houben-Weyl, Methoden der organischen Chemie (Methods of Organic Chemistry), vol. VIII/4, 230 et seq. (1968), and U.S. Pat. No. 4 948 899].

The ylidene compounds (IV) and (VII) are novel in the majority of cases, but can be prepared by conventional methods [cf. H. Dornow and W. Sassenberg, Liebigs Ann. Chem., 602, 14 (1957)].

The compounds of general formula (V) are also known [cf. N. Levy, C.W. Scaife, J. Chem. Soc. (London), 1946, 1100; C.D. Hurd, M.E. Nilson, J. Org. Chem., 20, 927 (1955)].

The aminocrotonic acid derivatives of formulae (VI) and (VIII) are known or can be prepared by known methods [S.A. Glickman, A.C. Cope, J. Am. Chem. Soc., 67, 1017 (1946); U.S. Pat. No. 4 948 899].

The above preparative processes are indicated solely by way of clarification. The preparation of the compounds of general formula (I) is not restricted to these processes, but every modification of these processes can be used in the same way for the preparation of the compounds according to the invention.

The compounds according to the invention exhibit a valuable pharmacological spectrum of action which could not have been predicted. They influence the contractility of the heart, the tonicity of the smooth muscles and the electrolyte and fluid balance.

They can therefore be used for the preparation of drugs for the treatment of pathologically modified blood pressure and cardiac insufficiency, and of coronary therapeutic agents.

They can also be used for the preparation of drugs for the treatment of diseases of the circulation and fluid balance, especially for the treatment of cardiac dysrhythmia, renal insufficiency, cirrhosis of the liver, ascites, pulmonary oedema, cerebral oedema, oedema of pregnancy, glaucoma or diabetes mellitus.

The cardiac and vascular actions were found on the isolated perfused guinea-pig heart. This is done using the hearts of guinea-pigs weighing 250 to 350 g. The animals are sacrificed by a blow to the head, the thorax is opened and a metal cannula is inserted into the exposed aorta. The heart together with the lungs are removed from the thorax and connected to the perfusion apparatus via an aortic cannula, with continuous perfusion. The lungs are severed at the roots. The perfusion medium used is a Krebs-Henseleit solution (1) (118.5 mmol/l NaCl, 4.75 mmol/l KCl, 1.19 mmol/l $KH_2PO_4$, 1.19 mmol/l $MgSO_4$, 25 mmol/l $NaHCO_3$, 0.013 mmol/l $Na_2EDTA$) with a $CaCl_2$ content of 1.2 mmol/1.10 mmol/l of glucose are added as the energy-providing substrate. Before perfusion, the solution is freed of particles by filtration. The solution is gassed with Carbogen (95% $O_2$, 5% $CO_2$) to maintain the pH at 7.4. The hearts are perfused at a constant flow rate (10 ml/min) at 32° C. by means of a squeezed roller pump.

To measure the heart function, a liquid-filled latex bag, which is connected to a pressure sensor via a liquid column, is inserted through the left atrium into the left ventricle and the isovolumetric contractions are recorded on a high-speed recorder (Opie, L., J. Physiol., 180 (1965), 529–541). The perfusion pressure is recorded by means of a pressure sensor connected to the perfusion system upstream of the heart. Under these conditions, a fall in the perfusion pressure indicates a coronary dilation and an increase or decrease in the left ventricular contraction amplitude indicates a fall or rise in the cardiac contractility., The compounds according to the invention are perfused into the perfusion system in suitable dilutions just upstream of the isolated heart.

Effects of the substances on the contraction amplitude of isolated guinea-pig atria at an active ingredient concentration of $10^{-6}$ g/ml

| Example no. | % change in the amplitude of ventricular pressure |
| --- | --- |
| 3 | −100% |
| 4 | −66% |

The novel active ingredients can be converted in known manner to the conventional formulations, such as tablets, coated tablets, pills, granules, aerosols, syrups, emulsions, suspensions and solutions, using inert, non-toxic, pharmaceutically acceptable excipients or solvents. Here the therapeutically active compound should be present in each case in a concentration of about 0.5 to 90% by weight of the total mixture, i.e. in amounts sufficient to attain the indicated dosage range.

The formulations are prepared for example by diluting the active ingredients with solvents and/or excipients, if necessary using emulsifiers and/or dispersants, it being possible, if appropriate, to use organic solvents as cosolvents, e.g. in the case where water is used as the diluent.

Administration is effected in conventional manner, preferably orally or parenterally and especially perlingually or intravenously.

In general, it has been found advantageous to administer amounts of about 0.001 to 1 mg/kg, preferably about 0.01 to 0.5 mg/kg of body weight, in the case of intravenous administration, in order to achieve effective results; in the case of oral administration, the dosage is about 0.01 to 20 mg/kg, preferably 0.1 to 10 mg/kg of body weight.

It may nevertheless be necessary to deviate from said amounts as a function of the body weight or the method of administration, the individual response to the drug, its formulation type and the time or interval at which it is administered. Thus it is possible in some cases to manage with less than the above-mentioned minimum amount, whereas in other cases said upper limit has to be exceeded. When larger amounts are administered, it may be advisable to divide them up into several single doses over the day.

STARTING COMPOUND

Example I 2-(N-Benzyl-N-methylamino)-ethyl 3-(3-phenyl-quinolin-5-ylidene)-2-oxo-butyrate

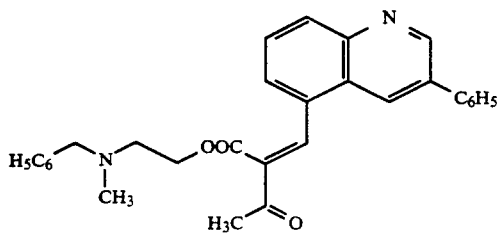

11.65 g (50 mmol) of 3-phenyl-quinolin-5-aldehyde are boiled overnight in 250 ml of methylene chloride with 12.5 g (50 mmol) of 2-(N-benzyl-N-methylamino)-ethyl 2-oxo-butyrate and a catalytic amount of piperidine acetate, using a water separator. The mixture is cooled, extracted twice by shaking with water, dried and concentrated. The crude product obtained is purified by flash chromatography with toluene/ethyl acetate mixtures to give 15.6 g (67.2% of theory) of a slightly coloured oil.

PREPARATORY EXAMPLES

Example 1

Dimethyl 1,4-dihydro-2,6-dimethyl-4-(3-phenyl-quinolin-5-yl)-pyridine-3,5-dicarboxylate

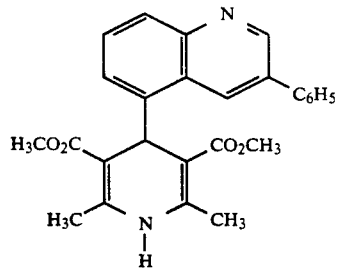

2.33 g (10 mmol) of 3-phenyl-quinolin-5-aldehyde are boiled for 16 hours in 20 ml of methanol with 2.3 g of methyl acetoacetate and 1.5 ml of 25% ammonia solution. A further 0.75 ml of ammonia is added and the mixture is boiled for 24 hours and cooled; the substance which has precipitated out is filtered off with suction and washed with a small amount of methanol to give 2.91 g of colourless crystals melting at 265° C.

EXAMPLE 2

3-[2-(N-Benzyl-N-methylamino)-ethyl 5-methyl 1,4-dihydro-2,6-dimethyl-4-(3-phenyl-quinolin-3,5-dicarboxylate

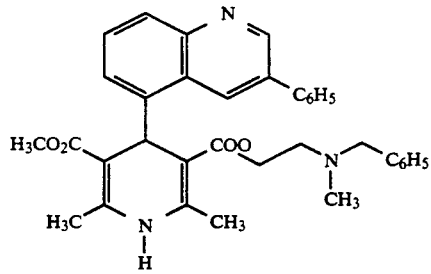

4.64 g (10 mmol) of the compound of Example I are refluxed for 18 hours in 20 ml of isopropanol with 1.15 g (10 mmol) of methyl 3-aminocrotonate. The mixture is cooled, concentrated and purified by flash chromatography with methylene chloride/ethyl acetate mixtures. The purified fractions are combined, concentrated and crystallised by stirring with acetonitrile. The crystals are filtered off with suction and washed with acetonitrile to give 3.3 g of a colourless substance melting at 169-171° C.

The Examples listed in Tables 1-5 are prepared analogously to the instructions of Examples 1 and 2:

TABLE 1

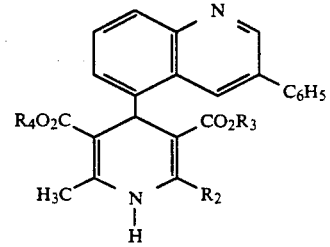

| Ex. no. | $R^2$ | $R^3$ | $R^4$ | M.p. °C. |
|---|---|---|---|---|
| 3 | —CH$_3$ | —C$_2$H$_5$ | —C$_2$H$_5$ | 268 |
| 4 | —CH$_3$ | —(CH$_2$)$_2$CN | —CH$_3$ | 199 |
| 5 | —CH$_3$ | —H | —CH$_3$ | 197 |
| 6 | —CH$_3$ | —(CH$_2$)$_2$CN | —CH(CH$_3$)$_2$ | 169 |
| 7 | —CH$_3$ | —(CH$_2$)$_2$CN | —C$_2$H$_5$ | 196 |
| 8 | —CH$_3$ | —H | —CH(CH$_3$)$_2$ | 146 |
| 9 | —CH$_3$ | —H | —C$_2$H$_5$ | 149 |
| 10 | —C$_2$H$_5$ | —C$_2$H$_5$ | —CH$_3$ | 220 |
| 11 | H | —C$_2$H$_5$ | —CH$_3$ | 253 |
| 12 | —CH$_3$ | —CH(CH$_3$)$_2$ | —CH$_3$ | 205 |
| 13 | —CH$_3$ | —(CH$_2$)$_2$OCH$_3$ | —CH(CH$_3$)$_2$ | 185 |
| 14 | —NH$_2$ | —CH$_3$ | —CH(CH$_3$)$_2$ | 233 |

TABLE 2

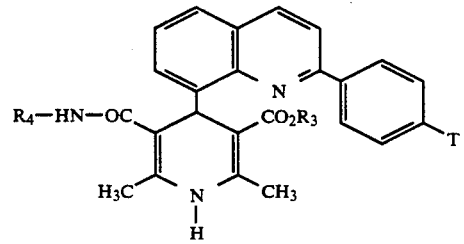

| Ex. no. | $R^3$ | $R^4$ | T | M.p. °C. |
|---|---|---|---|---|
| 15 | —(CH$_2$)$_2$—N(CH$_3$)—CH$_2$—C$_6$H$_5$ | |  | F | 209 |

TABLE 2-continued

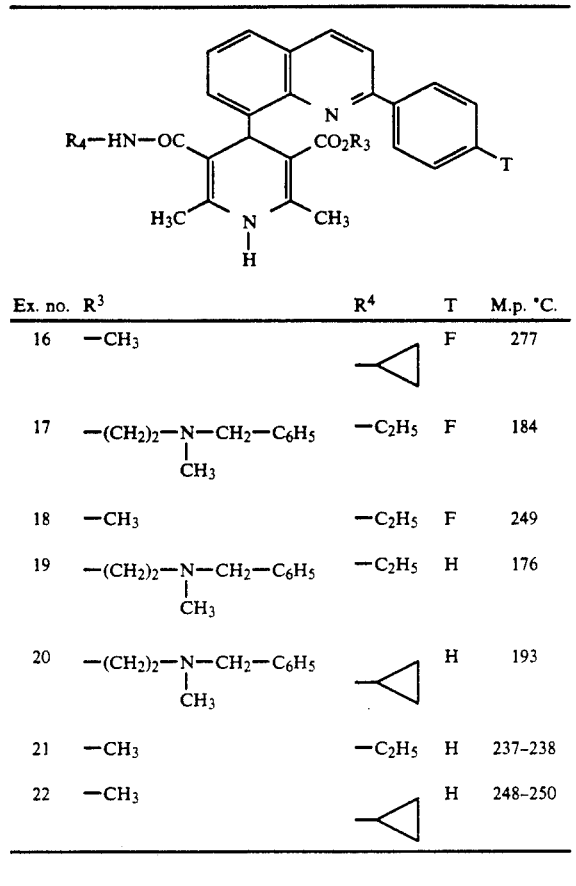

| Ex. no. | R³ | R⁴ | T | M.p. °C. |
|---|---|---|---|---|
| 16 | —CH₃ | cyclopropyl | F | 277 |
| 17 | —(CH₂)₂—N(CH₃)—CH₂—C₆H₅ | —C₂H₅ | F | 184 |
| 18 | —CH₃ | —C₂H₅ | F | 249 |
| 19 | —(CH₂)₂—N(CH₃)—CH₂—C₆H₅ | —C₂H₅ | H | 176 |
| 20 | —(CH₂)₂—N(CH₃)—CH₂—C₆H₅ | cyclopropyl | H | 193 |
| 21 | —CH₃ | —C₂H₅ | H | 237–238 |
| 22 | —CH₃ | cyclopropyl | H | 248–250 |

TABLE 3

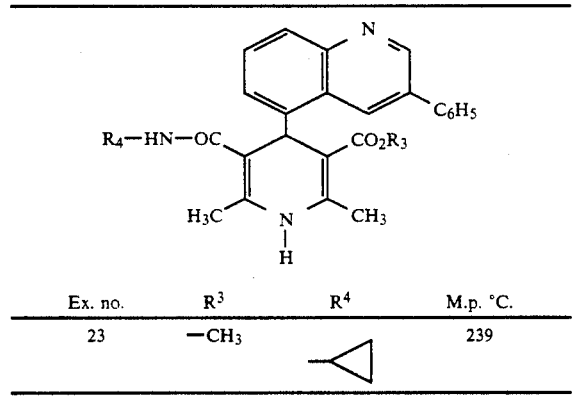

| Ex. no. | R³ | R⁴ | M.p. °C. |
|---|---|---|---|
| 23 | —CH₃ | cyclopropyl | 239 |

TABLE 4

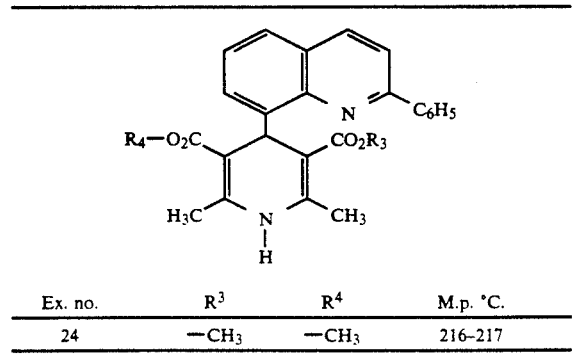

| Ex. no. | R³ | R⁴ | M.p. °C. |
|---|---|---|---|
| 24 | —CH₃ | —CH₃ | 216–217 |

TABLE 5

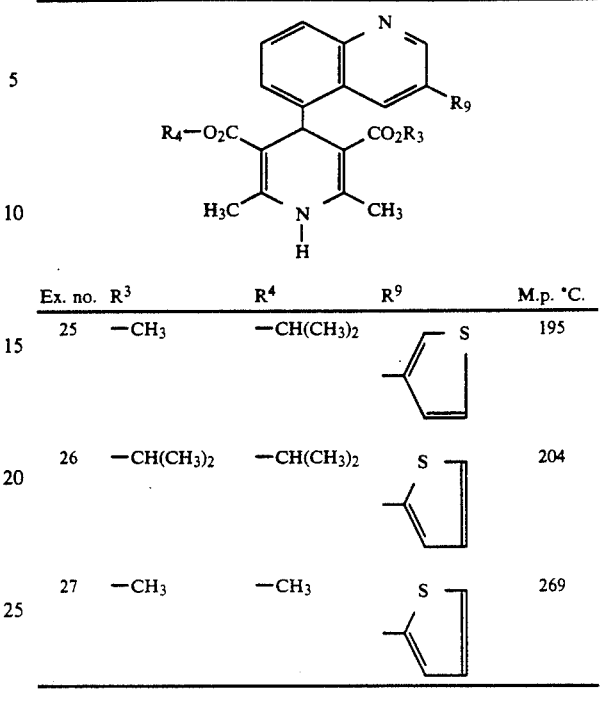

| Ex. no. | R³ | R⁴ | R⁹ | M.p. °C. |
|---|---|---|---|---|
| 25 | —CH₃ | —CH(CH₃)₂ | 2-thienyl | 195 |
| 26 | —CH(CH₃)₂ | —CH(CH₃)₂ | 2-thienyl | 204 |
| 27 | —CH₃ | —CH₃ | 2-thienyl | 269 |

TABLE 6

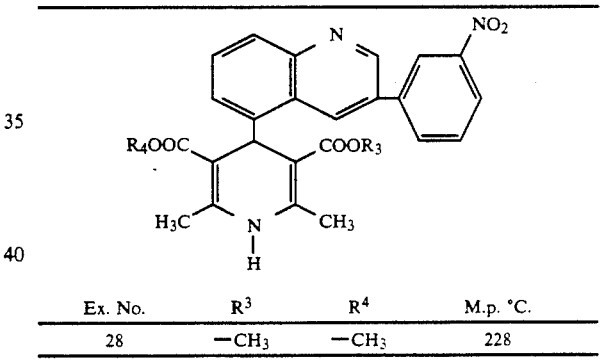

| Ex. No. | R³ | R⁴ | M.p. °C. |
|---|---|---|---|
| 28 | —CH₃ | —CH₃ | 228 |

We claim:
1. An aryl-quinolyl-substituted 1,4-dihydropyridine-dicarboxylic acid derivative of the formula (I):

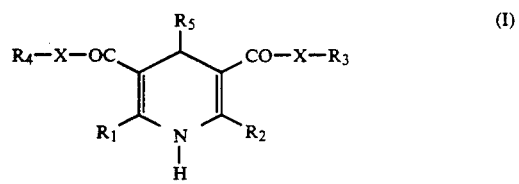

in which
R¹ and R² are identical or different and are hydrogen or linear or branched alkyl having up to 6 carbon atoms, or
one of the two substituents R¹ or R² is the —NH₂ group,
X is an oxygen atom or the —NH— group,
R³ and R⁴ are identical or different and are hydrogen or cycloalkyl having 3 or 6 carbon atoms, or are linear or branched alkenyl or alkyl each having up to 10 carbon atoms which may be interrupted by an oxygen or sulphur atom in the chain or which may be unsubstituted or substituted by carboxyl, halogen, cyano, hydroxyl, phenyl, phenoxy or benzyloxy, or by linear or branched alkoxy, acyl or alkoxycarbonyl each having up to 8 carbon atoms, or by a group of the formula —NR$^6$R$^7$, wherein R$^6$ and R$^7$ are identical or different and are hydrogen, linear or branched alkyl having up to 6 carbon atoms, benzyl or phenyl, and R$^5$ is a radical of the formula

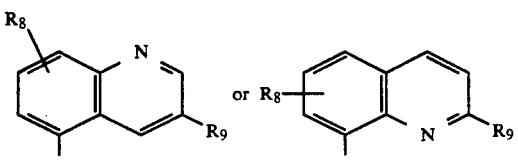

wherein

R$^8$ is hydrogen, halogen or linear or branched alkyl or alkoxy each having up to 6 carbon atoms, and R$^9$ is aryl having 6 to 10 carbon atoms which is unsubstituted or substituted by up to 3 identical or different substituents selected from the group comprising halogen nitro cyano, trifluoromethyl, trifluoromethoxy and trifluoromethylthio, or by linear or branched alkyl having up to 8 carbon atoms, which in turn can be substituted by aryl having 6 to 10 carbon atoms, or by linear or branched alkoxy or alkoxycarbonyl each having up to 8 carbon atoms, by carboxyl or by a group of the formula —NR$^6$R$^7$, wherein R$^6$ and R$^7$ are as defined above, or R$^9$ is 2- or 3-thienyl which is unsubstituted or substituted by halogen, or a physiologically acceptable salt thereof.

2. A compound or salt thereof according to claim 1 in which

R$^1$ and R$^2$ are identical or different and are hydrogen or linear or branched alkyl having up to 4 carbon atoms, or one of the two substituents R$^1$ R$^2$ is the —NH$_2$ group, X is an oxygen atom or the —NH— group, R$^3$ and R$^4$ are identical or different and are hydrogen, cyclopropyl, cyclopentyl or cyclohexyl, or are linear or branched alkenyl or alkyl each having up to 8 carbon atoms which may be interrupted by an oxygen or sulphur atom in the chain which may be unsubstituted or substituted by carboxyl, halogen, cyano, hydroxyl or phenyl, or by linear or branched alkoxy, acyl or alkoxycarbonyl each having up to 6 carbon atoms, or by a group of the formula —NR$^6$R$^7$, wherein R$^6$ and R$^7$ are identical or different and are hydrogen, linear or branched alkyl having up to 4 carbon atoms, or benzyl, and R$^5$ is a radical of the formula

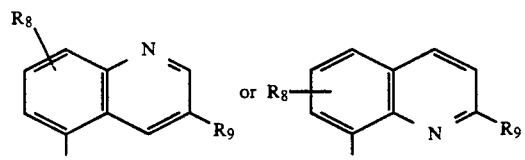

wherein

R$^8$ is hydrogen, halogen or linear or branched alkyl or alkoxy each having up to 4 carbon atoms, and R$^9$ is phenyl which is unsubstituted or substituted by up to 2 identical or different substituents selected from the group comprising halogen, nitro, cyano and trifluoromethyl, or by linear or branched alkyl or alkoxy each having up to 6 carbon atoms, by benzyl or by a group of the formula —NR$^6$R$^7$, wherein R$^6$ and R$^7$ are as defined above, or R$^9$ is 2- or 3-thienyl which is unsubstituted or substituted by halogen.

3. A compound or salt thereof according to claim 1 in which

R$^1$ and R$^2$ are identical different and are hydrogen, methyl, ethyl, propyl or isopropyl, or one of the two substituents R$^1$ or R$^2$ is the —NH$_2$ group, X is an oxygen atom or the —NH— group, R$^3$ and R$^4$ are identical or different and are hydrogen, cyclopropyl, cyclopentyl or linear or branched alkyl having up to 6 carbon atoms, which is unsubstituted or substituted by carboxyl, fluorine, chlorine, cyano or hydroxyl, or by linear or branched alkoxy, acyl or alkoxycarbonyl each having up to 4 carbon atoms, or by a group of the formula —NR$^6$R$^7$, wherein R$^6$ and R$^7$ are identical or different and are hydrogen, methyl, ethyl or benzyl, and R$^5$ is a group of the formula

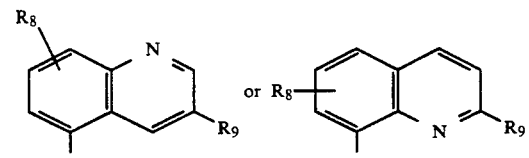

wherein

R$^8$ is hydrogen, ethyl or methyl, and

R$^9$ is phenyl which is unsubstituted or substituted by up to 2 identical or different substituents selected from the group comprising fluorine, chlorine, nitro and trifluoromethyl, or by linear or branched alkyl or alkoxy each having up to 4 carbon atoms, or by a group of the formula —NR$^6$R$^7$, wherein R$^6$ and R$^7$ are as defined above, or R$^9$ is 2- or 3-thienyl.

4. A compound according to claim 1, wherein such compound is diethyl 1,4-dihydro-2,6-dimethyl-4-(3-phenyl-quinolin-5-yl)-pyridine-3,5-dicarboxylate of the formula

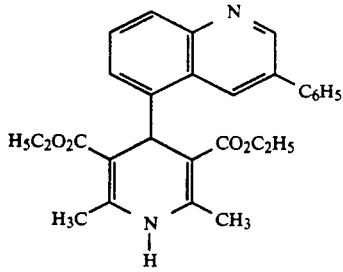

or a physiologically acceptable salt thereof.

5. A compound according to claim 1, wherein such compound is methyl cyanoethyl 1,4-dihydro-2,6dimethyl-4-(3-phenyl-quinolin-5-yl)-pyridine-3,5-dicarboxylate of the formula

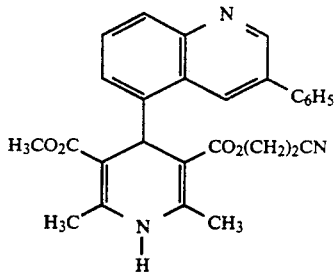

or a physiologically acceptable salt thereof.

6. A cardiovascular composition comprising a cardiovascular effective amount of a compound or salt according to claim 1 and a physiologically acceptable diluent.

7. A method of treating a cardiovascular condition in a patient suffering therefrom which comprises administering to such patient a cardiovascular effective amount of a compound or salt according to claim 1.

8. The method according to claim 7, wherein such compound is
diethyl 1,4-dihydro-2,6-dimethyl-4-(3-phenyl-quinolin-5yl)-pyridine-3,5-dicarboxylate or
methyl cyanoethyl 1,4-dihydro-2,6-dimethyl-4-(3-phenyl-quinolin-5-yl)-pyridine-3,5-dicarboxylate,
or a physiologically acceptable salt thereof.

* * * * *